US012616448B2

(12) United States Patent
Shahriari Shourabi et al.

(10) Patent No.: US 12,616,448 B2
(45) Date of Patent: May 5, 2026

(54) METHODS AND SYSTEMS FOR AUTOMATED ANALYSIS OF CERVIX ELASTOGRAPHY

(71) Applicant: GE Precision Healthcare LLC, Waukesha, WI (US)

(72) Inventors: Mostafa Shahriari Shourabi, Upper Austria (AT); Christian Perrey, Upper Austria (AT)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 391 days.

(21) Appl. No.: 18/485,124

(22) Filed: Oct. 11, 2023

(65) Prior Publication Data

US 2025/0120675 A1    Apr. 17, 2025

(51) Int. Cl.
*A61B 8/00*     (2006.01)
*G06T 7/00*     (2017.01)

(52) U.S. Cl.
CPC ............ *A61B 8/485* (2013.01); *A61B 8/5223* (2013.01); *G06T 7/0012* (2013.01); *G06T 2207/10132* (2013.01); *G06T 2207/30081* (2013.01)

(58) Field of Classification Search
CPC ....... A61B 8/485; A61B 8/5223; A61B 8/085; A61B 8/469; G06T 7/0012; G06T 2207/10132; G06T 2207/30081; G06T 2207/10016; G06T 2207/30044
See application file for complete search history.

(56) References Cited

U.S. PATENT DOCUMENTS

2021/0192718 A1*    6/2021    Brandl .................... A61B 5/004
2022/0230310 A1*    7/2022    Xie ........................... G06T 7/12

OTHER PUBLICATIONS

Hee et al.: "Quantitative sonoelastography of the uterine cervix prior to induction of labor as a predictor of cervical dilation time"; 2014; AOGS ACTA Obstetricia et Gynecologica Scandinavica; pp. 684-690. (Year: 2014).*
Dudea-Simon et al.: "Usefulness of real time elastography strain ratio in the assessment of cervical intraepithelial neoplasia and cervical cancer using a reference material", 202; Med Ultrason; vol. 22, No. 2; pp. 145-151. (Year: 2020).*
Hernandez-Andrade, E. et al., "Cervical strain determined by ultrasound elastography and its association with spontaneous preterm delivery," Journal of Perinatal Medicine, vol. 42, No. 2, Mar. 2014, 20 pages.
Köbbing, K et al., "Quantitative elastography of the uterine cervix as a predictor of preterm delivery," Journal of Perinatology, vol. 34, No. 10, Oct. 2014, Available Online May 8, 2014, 7 pages.
Swiatkowska-Freund, M et al., "Cervical elastography during pregnancy: clinical perspectives," International Journal of Women's Health, vol. 9, Apr. 21, 2017, 10 pages.

(Continued)

*Primary Examiner* — Siamak Harandi
(74) *Attorney, Agent, or Firm* — McCoy Russell LLP

(57) ABSTRACT

Various methods and systems are provided for cervix elastographic analysis. In one embodiment, the method comprises acquiring an ultrasound scene comprising a plurality of frames, generating a first loss image for the plurality of frames, selecting a background and a foreground of the ultrasound scene based on the first loss image, and generating a softness ratio from the selected background and foreground.

20 Claims, 10 Drawing Sheets

(56)     References Cited

OTHER PUBLICATIONS

Wang, B. et al., "Diagnostic accuracy of cervical elastography in predicting preterm delivery: A systematic review and meta-analysis," Medicine (Baltimore), vol. 98, No. 29, Jul. 2019, 9 pages.

"Bishop Score," Cleveland Clinic Website, Available Online at https://my.clevelandclinic.org/health/diagnostics/24252-bishop-score, Available as Early as Jan. 29, 2023, 11 pages.

Abdallah, Y. et al., "Value of cervical strain in ultrasound elastography as a predictor of spontaneous preterm delivery," Egyptian Journal of Radiology and Nuclear Medicine, vol. 54, No. 39, Feb. 20, 2023, 16 pages.

* cited by examiner

400

METHODS AND SYSTEMS FOR AUTOMATED ANALYSIS OF CERVIX ELASTOGRAPHY

FIELD

Embodiments of the subject matter disclosed herein relate to an automated approach to analyzing cervix elastography such as for assessing likelihood of pre-term birth.

BACKGROUND

Clinical ultrasound is an imaging modality that employs ultrasound waves to probe the internal structures of a body of a patient and produce a corresponding image. An ultrasound probe comprising a plurality of transducer elements emits ultrasonic pulses which reflect or echo, refract, or are absorbed by structures in the body. The ultrasound probe then receives reflected echoes, which are processed into an image. For example, a medical imaging device such as an ultrasound imaging device may be used to obtain images of a heart, uterus, liver, lungs, and various other anatomical regions of a patient.

One application of clinical ultrasound is elastography. Elastography seeks to evaluate the mechanical properties of tissues, particularly their stiffness and elasticity, by analyzing how they respond to external forces or physiological processes. One of the key parameters in elastography is strain, which quantifies the percentage of tissue deformation that occurs when static or oscillatory compression is applied. The strain metric measures tissue deformation under pressure, with softer tissues deforming more readily, resulting in larger strain values. Conversely, stiffer tissues exhibit reduced deformation, leading to lower strain values.

Cervix elastography is one approach for predicting pre-term birth. During cervix elastography, an ultrasound technician selects cervical tissue of interest and reference tissue of an ultrasound image, referred to as a foreground and a background, respectively, and calculates strain values to obtain a softness ratio of the cervix tissue. The softness ratio is used to assess cervical changes that may be indicative of pre-term labor. Shear wave imaging analysis is an alternative approach for predicting pre-term birth. However, the shear wave method utilizes a high energy push pulse, which may be transmitted to a region close to the head of the fetus.

BRIEF DESCRIPTION

In one embodiment, a method comprises acquiring an ultrasound scene comprising a plurality of frames, generating a first loss image for the plurality of frames, selecting a background and a foreground of the ultrasound scene based on the first loss image, and generating a softness ratio from the selected background and foreground.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
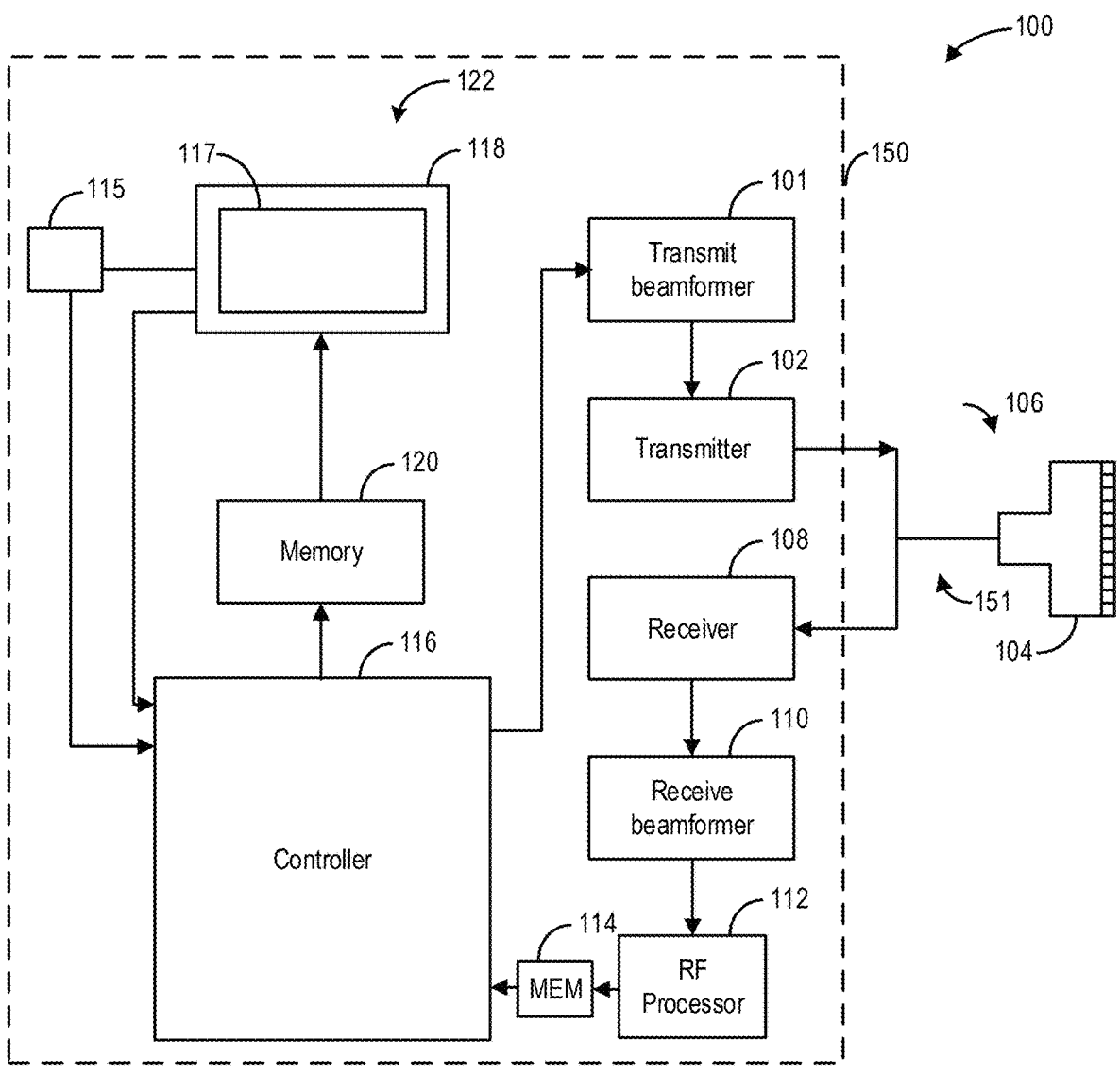
FIG. 1 shows an ultrasound imaging system, according to one or more embodiments of the present disclosure.

The following description relates to various embodiments of systems and methods for automated cervix elastography. Predicting pre-term birth is an application of cervix elastography. As clinically practiced, an ultrasound technician performs a cervical ultrasound, selecting from the ultrasound image a foreground region and a background region of the cervix (also herein, a foreground and a background). The foreground region may represent cervical tissue of interest, and the background region may represent baseline tissue with which to compare the cervical tissue of interest for estimating changes in cervical elasticity. Strain values are obtained for the selected regions, where the strain values are measurements of a deformation or displacement of tissue structures in response to an applied mechanical force or stress. The strain values are used to obtain a softness ratio indicating the softness of the cervix tissue. The softness ratio may be used to assess cervical changes that may be indicative of pre-term labor.

Currently, selecting the foreground region and background region of the cervix is entirely manual, which presents challenges for the clinical practice of cervical elastography. As one example, reliance on user input may produce erroneous output due to the instability of the cervix elastography, and a variability of the technique as pertains to the expertise of the technician. Relatedly, manual selection of the background region and the foreground region may be difficult for an inexperienced technician. Further, as currently practiced, cervical elastographic analysis is performed on a user-selected frame of the ultrasound imaging data, increasing the complexity for the technician and possibility of a wrong output. Another challenge, for even highly-skilled technicians, is that manual selection of the background region and foreground region is time-consuming process.

To address the aforementioned challenges, disclosed herein is an approach for automating cervical elastographic analysis. In the disclosed approach, the ultrasound technician (also herein, a user) guides the cervical elastographic analysis by indicating a position of a cervix on a cervical ultrasound scene (also herein, a scene) produced during cervical ultrasound imaging. As used herein the cervical ultrasound scene comprises a digital recording that captures real-time images or frames produced during a cervical ultrasound exam. In some examples, the indication may comprise the user drawing a line or a rectangle containing the cervix area on the cervical ultrasound scene, such as via a user input device coupled to an ultrasound imaging system. The approach includes automatically analyzing a portion of the entire scene (e.g., all frames of the scene) proximate to the user-guided cervix area using a strain measurement to calculate a loss image, and proposing a foreground and a background to the user based on the loss image. In some examples, a first loss image may be generated by calculating a mean and standard deviation of the measured strain over a sequence of images, or in other words, by averaging over frames in a temporal direction. Additionally, or alternatively, several loss images may be generated. In some examples, the user may confirm the selection, and, in response to the user confirmation, the approach includes automatically generating a softness ratio based on the automatically-selected regions by averaging the softness ratio of foreground and background strain measurements across the entire scene.

By automating the selection of the foreground and the background of the cervical ultrasound scene based on the loss image, a number of advantages are realized. The loss image increases processing efficiency by focusing the analysis on tissues within proximity of the user-guided cervix area. Further, using the loss image may be more efficient by generating the softness ratio from the automatically-selected foreground and the background, rather than the entire scene. The processing efficiency gains of the approach support increased accuracy, as the selection of the foreground and background regions, and the measurements performed thereon, may be more accurate due to the analysis of the all frames of the cervical ultrasound scene. The approach reduces reliance on technician experience, and further, as a benefit to experts and less-experienced technicians, the approach reduces effort and time to perform cervical elastography. As another advantage, the disclosed approach is compatible with shear wave imaging as a method for automatically determining a background and a foreground in shear wave analyses. However, the disclosed approach may also replace shear wave analysis when a less invasive approach is desired. Strain imaging does not utilize such a high energy push pulse to determine elastic properties of the cervical tissue, and is therefore preferable to shear wave imaging for predicting pre-term birth. In this way, the disclosed approach increases usability, increases efficiency, reduces the effect of noisy measurements, reduces a reliance on expert-level knowledge, and is less invasive to the fetus.

Figure 2:
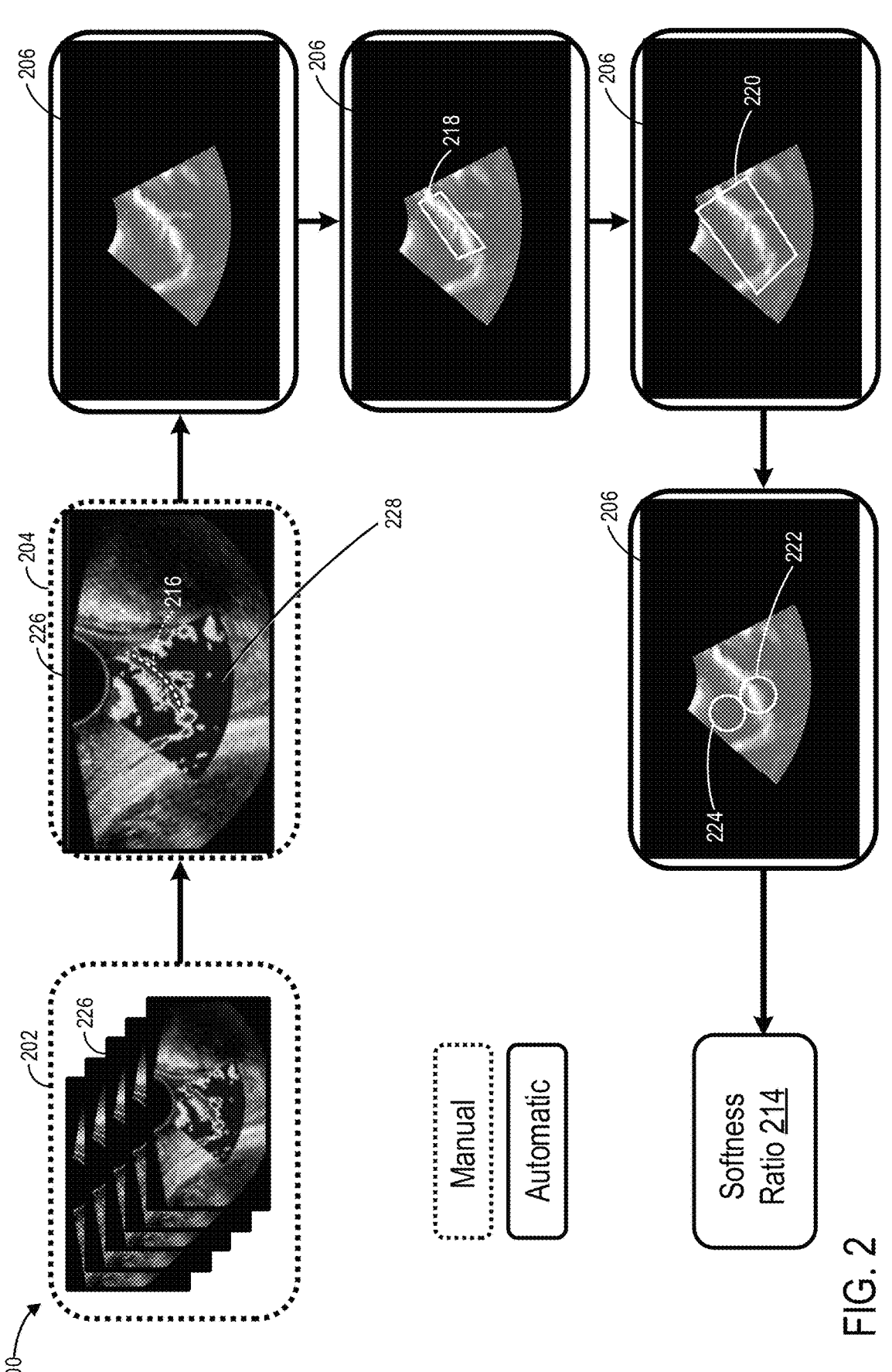
FIG. 2 shows an overview of a process for automated analysis of cervix elastography according to an exemplary embodiment.

Methods and systems are provided herein for automated analysis of cervix elastography using an ultrasound imaging system, such as the system 100 of FIG. 1. A diagram illustrating the disclosed approach for automated analysis of cervical elastography using an ultrasound imaging system is shown in FIG. 2. The ultrasound imaging system may execute one or more methods for cervical elastography, which are shown by flow charts illustrating methods 300,

4

Figure 3:
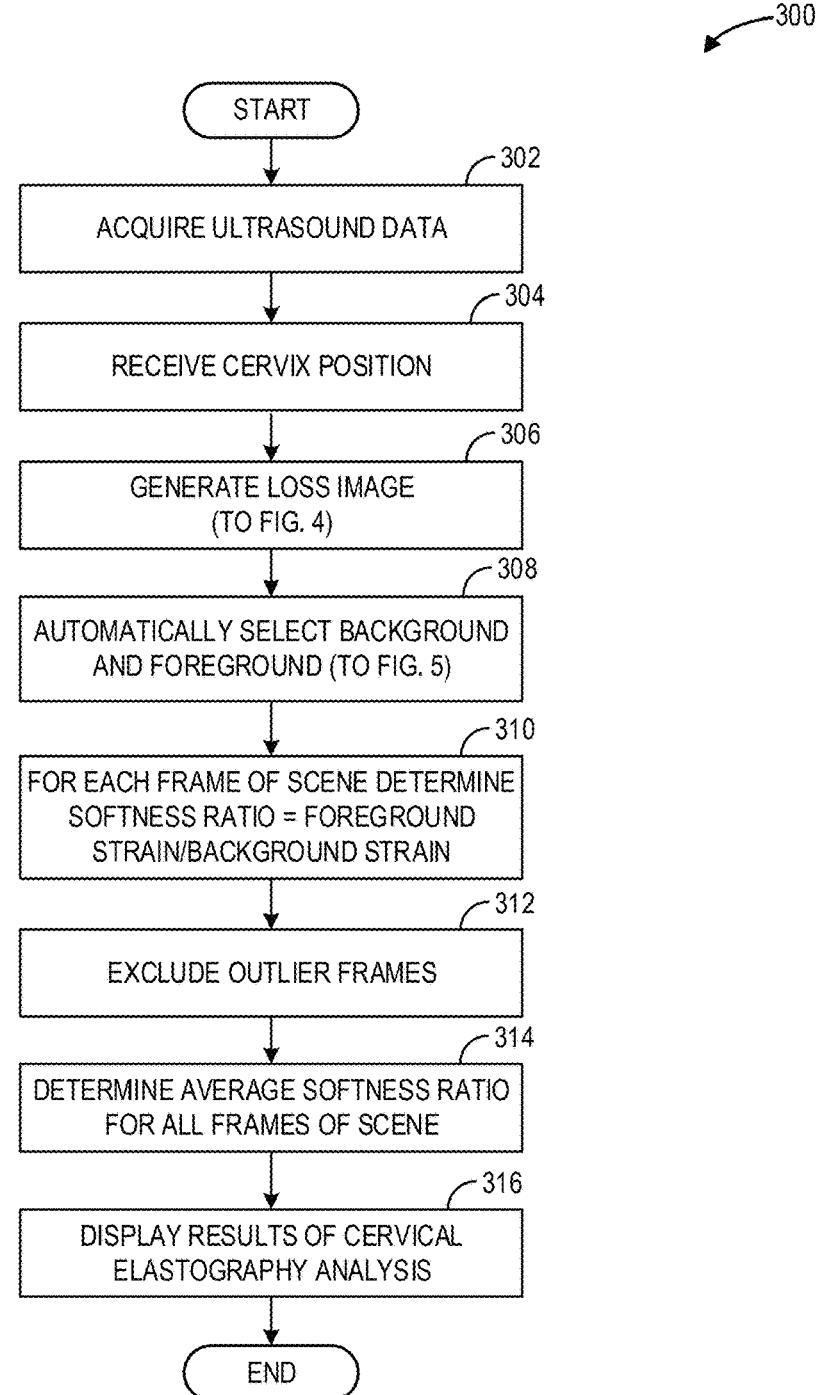
FIG. 3 shows a flow chart illustrating a first method for automated analysis of cervix elastography according to an exemplary embodiment.
Figure 4:
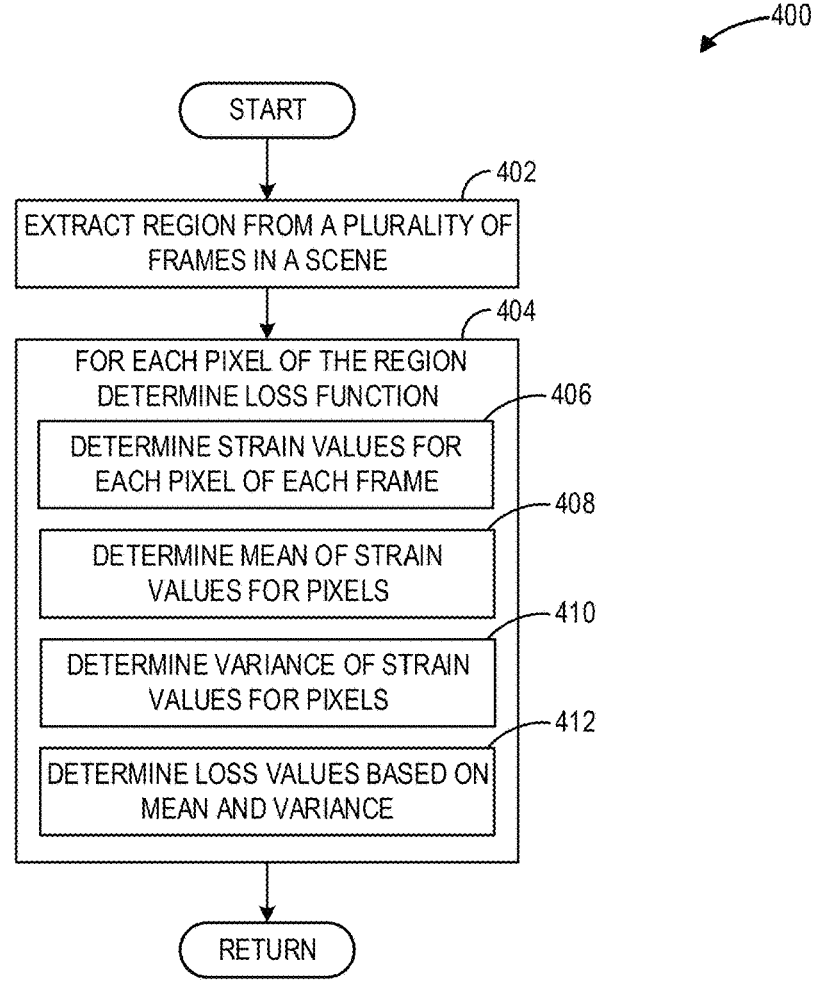
FIG. 4 shows a flow chart illustrating a second method for automated analysis of cervix elastography according to an exemplary embodiment.
Figure 5:
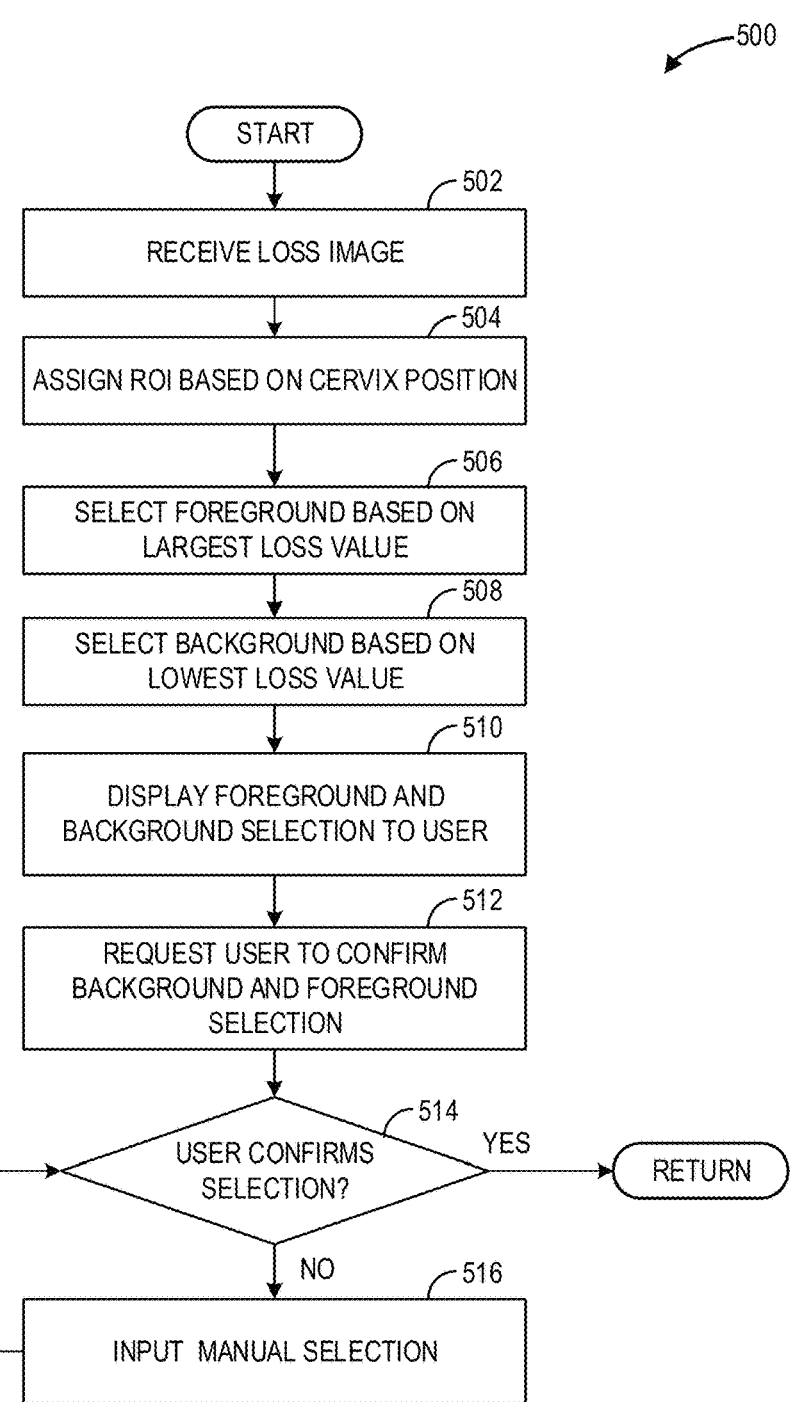
FIG. 5 shows a flow chart illustrating a third method for automated analysis of cervix elastography according to an exemplary embodiment.
Figure 6:
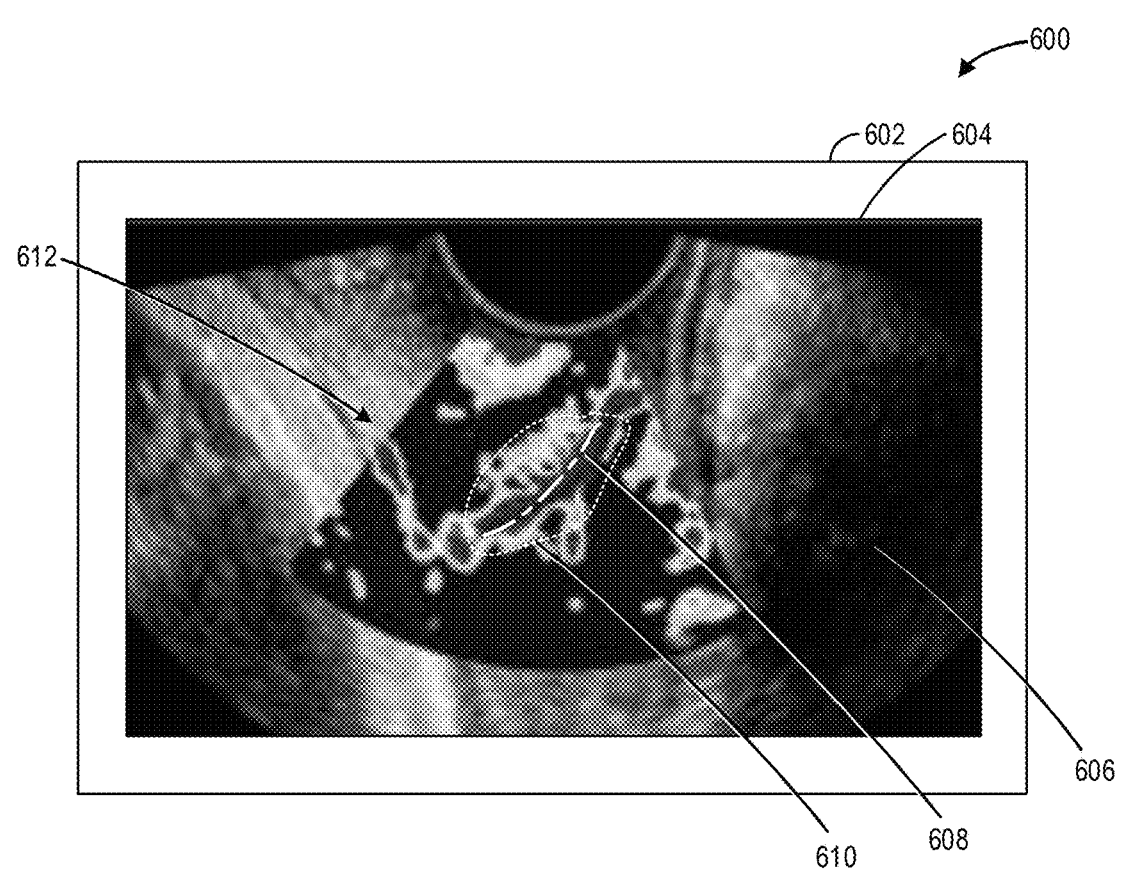
FIG. 6 shows a display device displaying a frame of a cervical ultrasound scene including user input according to an exemplary embodiment.
Figure 7:
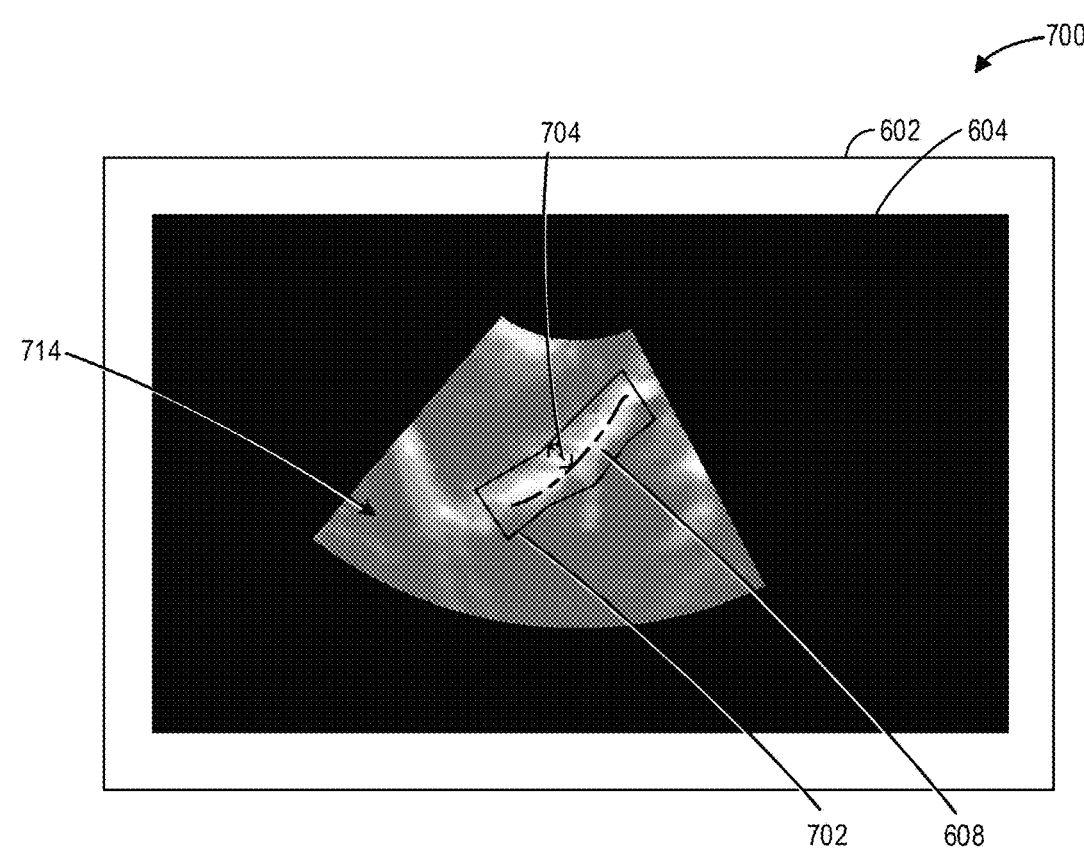
FIG. 7 shows a display device displaying a loss image generated for a cervical ultrasound scene including automated foreground region of interest assignment according to an exemplary embodiment.
Figure 8:
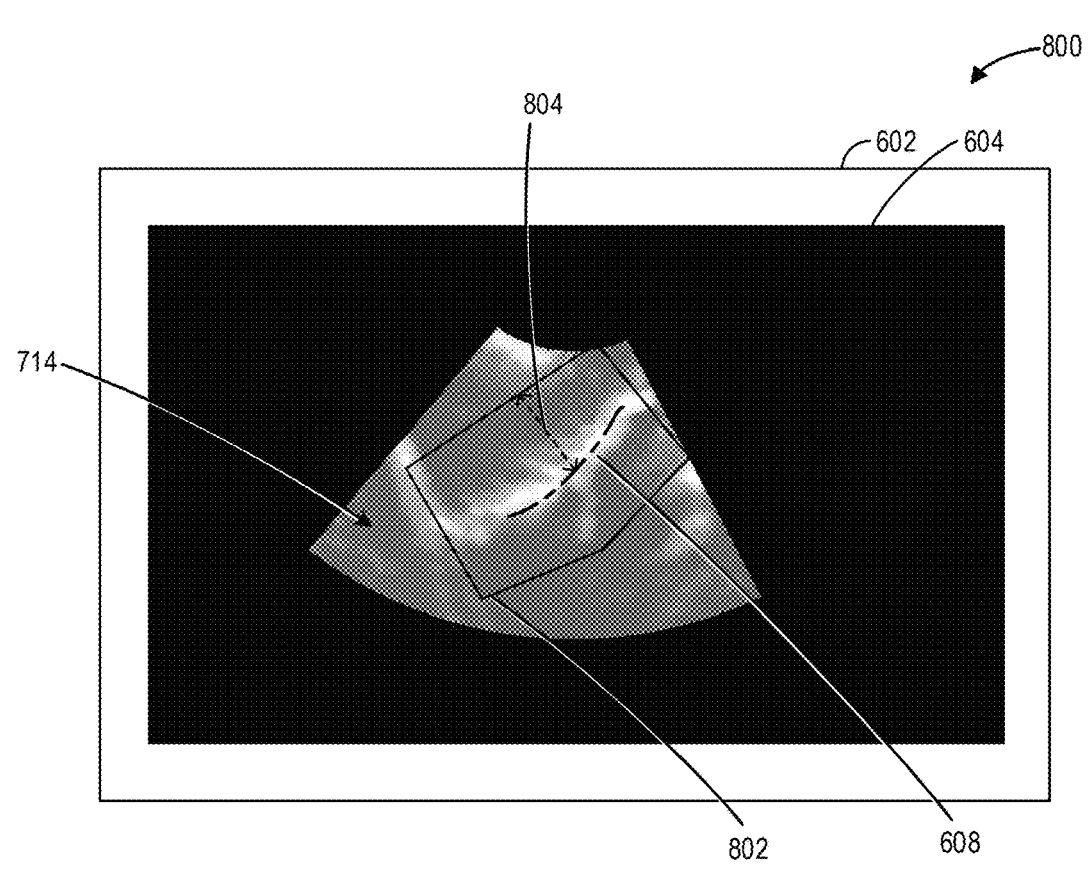
FIG. 8 shows a display device displaying a loss image generated for a cervical ultrasound scene including automated background region of interest assignment according to an exemplary embodiment.
Figure 9:
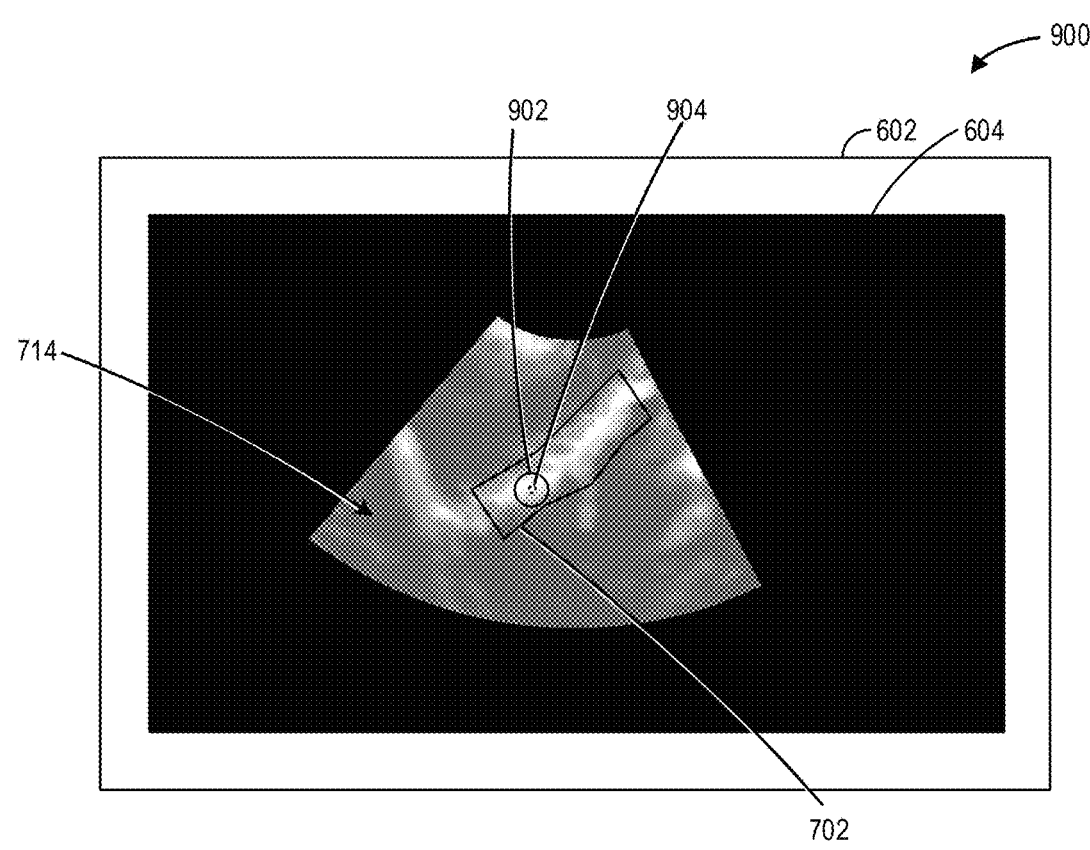
FIG. 9 shows a display device displaying a loss image generated for a cervical ultrasound scene including automated foreground selection according to an exemplary embodiment.
Figure 10:
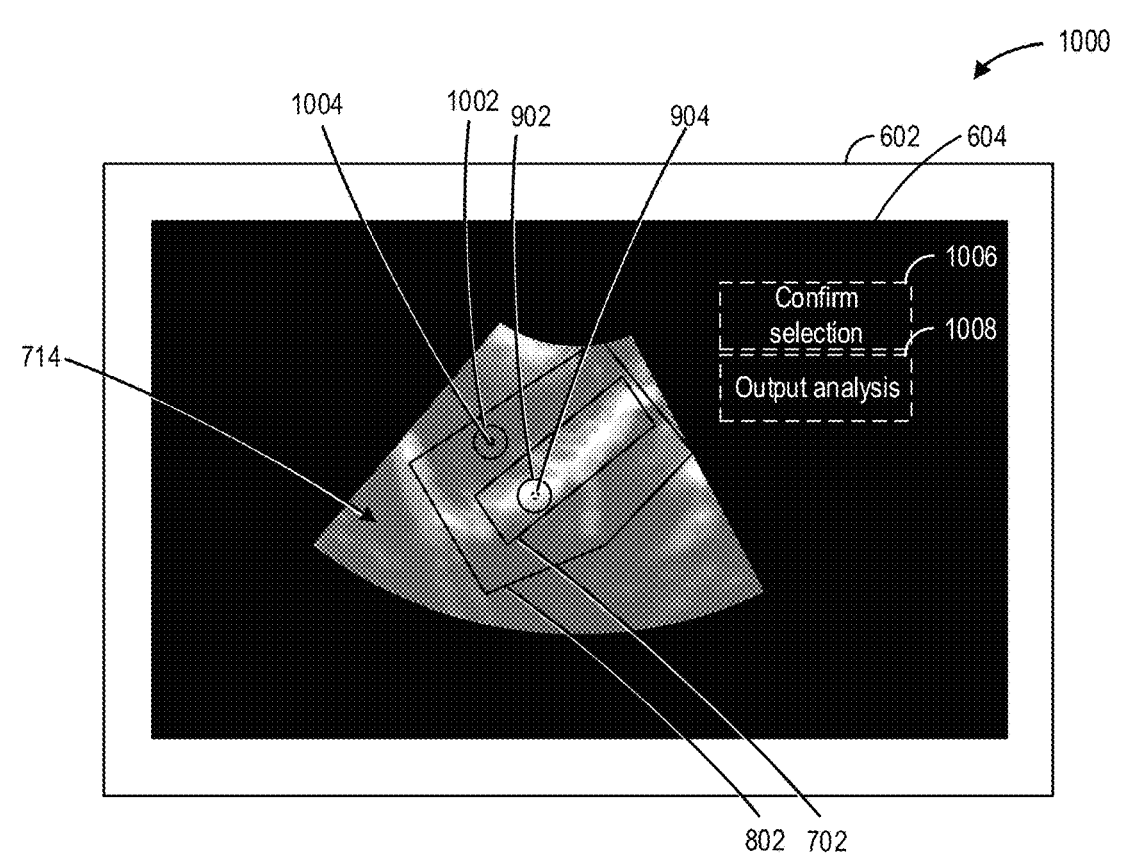
FIG. 10 shows a display device displaying a loss image generated for a cervical ultrasound scene including automated background selection according to an exemplary embodiment.

400, and 500, shown in FIGS. 3, 4, and 5, respectively. In the disclosed approach, an operator guides an automated cervical elastography analysis by indicating a cervix position on an ultrasound scene. The automated cervical elastography analysis analyzes the entire scene and generates a cervical elastography analysis output. A display showing an example ultrasound scene including an operator-indicated cervix position as part of an automated cervical elastographic analysis is shown in FIG. 6. The display of FIG. 6 including foreground region of interest selection as part of an automated cervical elastographic analysis is shown in FIG. 7. The display of FIG. 6 including background region of interest selection as part of an automated cervical elastographic analysis is shown in FIG. 8. The display of FIG. 6 including foreground selection as part of an automated cervical elastographic analysis is shown in FIG. 9. The display of FIG. 6 including background selection as part of an automated cervical elastographic analysis is shown in FIG. 10. In some examples, the systems and methods for automated cervical elastography disclosed herein may be applied to elastographic analysis of other tissues and organs, such as breast imaging.

FIG. 1 depicts a block diagram of a system 100 according to one embodiment. In the illustrated embodiment, the system 100 is an imaging system and, more specifically, an ultrasound imaging system. As shown, the system 100 includes multiple components. The components may be coupled to one another to form a single structure, may be separate but located within a common room, or may be remotely located with respect to one another. For example, one or more of the modules described herein may operate in a data server that has a distinct and remote location with respect to other components of the system 100, such as a probe and user interface. Optionally, in the case of ultrasound systems, the system 100 may be a unitary system that is capable of being moved (e.g., portably) from room to room. For example, the system 100 may include wheels or be transported on a cart.

In the illustrated embodiment, the system 100 includes a transmit beamformer 101 and transmitter 102 that drives an array of elements 104, for example, piezoelectric elements including piezoceramics, high-dielectric ceramics, single crystals, etc., within a diagnostic ultrasound probe 106 (or transducer) to emit ultrasonic signals (e.g., continuous or pulsed) into a body or volume (not shown) of a subject. The elements 104 and the probe 106 may have a variety of geometries. The ultrasonic signals are back-scattered from structures in a body, for example, an inserted needle, to produce echoes that return to the elements 104. The echoes are received by a receiver 108. The received echoes are provided to a receive beamformer 110 that performs beamforming and outputs a radio frequency (RF) signal. The RF signal is then provided to an RF processor 112 that processes the RF signal. Alternatively, the RF processor 112 may include a complex demodulator (not shown) that demodulates the RF signal to form I/Q data pairs representative of the echo signals. The RF or I/Q signal data may then be provided directly to a memory 114 for storage (for example, temporary storage). The system 100 also includes a system controller 116 that may be part of a single processing unit (e.g., processor) or distributed across multiple processing units. The system controller 116 is configured to control operation of the system 100.

For example, the system controller 116 may include an image-processing module that receives image data (e.g., ultrasound signals in the form of RF signal data or I/Q data pairs) and processes image data. For example, the image-processing module may process the ultrasound signals to generate two-dimensional (2D) slices or frames of ultrasound information (e.g., ultrasound images) or ultrasound waveforms (e.g., continuous or pulse wave Doppler spectrum or waveforms) for displaying to the operator. The image-processing module may be configured to perform one or more processing operations according to a plurality of selectable ultrasound modalities on the acquired ultrasound information. By way of example only, the ultrasound modalities may include color-flow, acoustic radiation force imaging (ARFI), B-mode, A-mode, M-mode, spectral Doppler, acoustic streaming, tissue Doppler module, C-scan, and elastography. Further, in some examples, the one or more processing operations may include one or more image transforms, such as a Radon transform for identifying linear features in the ultrasound images.

Acquired ultrasound information may be processed in real-time during an imaging session (or scanning session) as the echo signals are received. Additionally or alternatively, the ultrasound information may be stored temporarily in the memory 114 during an imaging session and processed in less than real-time in a live or off-line operation. An image memory 120 is included for storing processed slices or waveforms of acquired ultrasound information that are not scheduled to be displayed immediately. The image memory 120 may comprise any known data storage medium, for example, a permanent storage medium, removable storage medium, and the like. Additionally, the image memory 120 may be a non-transitory storage medium including instructions that when executed cause the processor 112 to execute automated analysis of cervix elastography. For example, the instructions may cause the processor 112 to acquire an ultrasound scene comprising a plurality of frames and receive a user input indicating a cervix position on the ultrasound scene. The instructions may cause the processor 112 to generate a first loss image for the plurality of frames and select a background and a foreground of the ultrasound scene based on the first loss image. The instructions may cause the processor 112 to generate a softness ratio from the selected background and foreground. The approach for automated analysis of cervix elastography are described in more detail below with reference to FIGS. 2-10.

In operation, an ultrasound system may acquire data, for example, 2D data sets, spectral Doppler data sets, and/or volumetric data sets by various techniques (for example, three-dimensional (3D) scanning, real-time 3D imaging, volume scanning, 2D scanning with probes having positioning sensors, freehand scanning using a voxel correlation technique, scanning using 2D or matrix array probes, and the like). Ultrasound spectrum (e.g., waveforms) and/or images may be generated from the acquired data (at the controller 116) and displayed to the operator or user on the display device 118.

The system controller 116 is operably connected to a user interface 122 that enables an operator to control at least some of the operations of the system 100. The user interface 122 may include hardware, firmware, software, or a combination thereof that enables an individual (e.g., an operator) to directly or indirectly control operation of the system 100 and the various components thereof. As shown, the user interface 122 includes a display device 118 having a display area 117. In some embodiments, the user interface 122 may also include one or more user interface input devices 115, such as a physical keyboard, mouse, and/or touchpad. In one embodiment, a touchpad may be configured to the system controller 116 and display area 117, such that when a user moves a finger/glove/stylus across the face of the touchpad, a cursor atop the ultrasound image or Doppler spectrum on the display device 118 moves in a corresponding manner.

In an exemplary embodiment, the display device 118 is a touch-sensitive display (e.g., touchscreen) that can detect a presence of a touch from the operator on the display area 117 and can also identify a location of the touch in the display area 117. The touch may be applied by, for example, at least one of an individual's hand, glove, stylus, or the like. As such, the touch-sensitive display may also be characterized as a user input device that is configured to receive inputs from the operator (such as a request to adjust or update an orientation of a displayed image). The display device 118 also communicates information from the controller 116 to the operator by displaying the information to the operator. The display device 118 and/or the user interface 122 may also communicate audibly. The display device 118 is configured to present information to the operator during or after the imaging or data acquiring session. The information presented may include ultrasound images, graphical elements, measurement graphics of the displayed images, user-selectable elements, user settings, and other information (e.g., administrative information, personal information of the patient, and the like). In one example, ultrasound images may comprise an ultrasound scene (or video) comprising a plurality of 2D frames.

In addition to the image-processing module, the system controller 116 may also include one or more of a graphics module, an initialization module, a tracking module, and an analysis module. The image-processing module, the graphics module, the initialization module, the tracking module, and/or the analysis module may coordinate with one another to present information to the operator during and/or after the imaging session. For example, the image-processing module may be configured to display an acquired image on the display device 118, and the graphics module may be configured to display designated graphics along with the displayed image, such as selectable icons (e.g., image rotation icons) and measurement parameters (e.g., data) relating to the image. As one example, the analysis module may include an automated analysis of cervical elastography, described in more detail herein with reference to FIGS. 2-10.

The screen of a display area 117 of the display device 118 is made up of a series of pixels which display the data acquired with the probe 106. The acquired data includes one or more imaging parameters calculated for each pixel, or group of pixels (for example, a group of pixels assigned the same parameter value), of the display, where the one or more calculated image parameters includes one or more of an intensity, velocity (e.g., blood flow velocity), color flow velocity, texture, graininess, contractility, deformation, rate of deformation value, and strain, strain value. The series of pixels then make up the displayed image and/or Doppler spectrum generated from the acquired ultrasound data.

In some examples, an ultrasound console 150 may house the RF processor 112, the memory 114, the one or more user interface input devices 115, the system controller 116, the image memory 120, and the user interface 122 (including the display device 118 with the display area 117). The ultrasound console 150 may further house the transmit beamformer 101, the transmitter 102, the receiver 108, and the receive beamformer 110. Further, in some examples, a cable 151 may communicatively couple the probe 106 to the console 150, such that received ultrasound data may be transmitted from the probe 106 to the console 150 via the cable 151. In other embodiments not depicted at FIG. 1, the probe 106 may be communicatively coupled to the console 150 via one or more wireless networks. Thus, transmission of data and signals between the probe 106 and the console 150 for generating and interpreting ultrasound images may be enabled via the cable 151 or the one or more wireless networks.

FIG. 2 schematically illustrates a summary of a process 200 for automated cervical elastography, which is described in greater detail in reference to FIGS. 3, 4, and 5. The process 200 comprises an automatic approach for obtaining a foreground and a background for cervix elastographic analysis, including obtaining strain measurements for the cervix tissue, and generating a softness index therefrom. The foreground may represent cervical tissue of interest and the background may represent baseline or reference tissue with which to compare the cervical tissue of interest for estimating changes in cervical elasticity. The process 200 analyzes an entire ultrasound scene, e.g., all frames of the scene, as opposed to analyzing a single frame only. The process 200 includes manual sub-processes and automated sub-processes, as indicated below. In contrast with existing approaches, the disclosed approach illustrated by the process 200 automates steps of cervical elastographic analysis that are otherwise performed manually by an ultrasound technician.

The process 200 includes acquisition of a cervical ultrasound scene 202. The cervical ultrasound scene 202 is acquired manually by the ultrasound technician. For example, the ultrasound technician may operate a probe of an ultrasound imaging system, such as the probe 106 of system 100, to acquire the cervical ultrasound scene 202. In one example, the technician may execute a patient exam according to an exam workflow that dictates certain measurements of the cervix, including images of the cervix for structural assessments, and measurements of cervical tissue in response to compression. The cervical ultrasound scene 202 may comprise a plurality of frames 226. The cervical ultrasound scene 202 may be displayed to the ultrasound technician via a display device, such as the display device 118 of system 100.

A cervix position 216 may be manually marked by the ultrasound technician in one or more frames 226, as shown in a marked image 204.

Next, the process 200 includes automatic generation of a loss image 206 for a strain region of interest (ROI) 228 of the cervical ultrasound scene 202. In strain imaging, strain is measured in the strain ROI 228 and displayed as a color-coded representation. The color-coded representation of the measured strain may be overlaid on a brightness mode or "B mode" ultrasound image, where in the B-mode echoes generated by the ultrasound are represented as varying shades of gray. The loss image 206 may be calculated based on a loss function and the color-coded strain values in the strain ROI 228. Areas outside of the strain ROI 228 are not considered in the process 200. In one example, the loss image 206 may be at least a first loss image. Loss image calculation is described in greater detail below in reference to FIG. 3.

The process 200 includes automatic determination of a foreground region of interest 218 within loss image 206. The foreground region of interest 218 may be an area of the loss image 206 within a threshold proximity of the cervix position 216.

Similarly, the process 200 includes automatic determination of a background region of interest 220 of loss image 206. The background region of interest 220 may be a second area of the loss image 206 within a threshold proximity of the cervix position 216, which may comprise a larger region around, or at a greater distance from the cervix position 216 than the foreground region of interest 218. Alternatively, the background region of interest may be a selected as a region of a predetermined size that represents the area with the minimal loss function.

The process 200 then includes automatic selection of a foreground 222 and a background 224 from the foreground region of interest 218 and the background region of interest 220, respectively. The foreground 222 and the background 224 are automatically selected based on the loss image. The process of selection is described in more detail below with reference to FIGS. 3-5.

From the foreground 222 and the background 224, the process 200 includes automatic generation of a softness ratio 214. The generation of the softness ratio 214 is described below in reference to FIGS. 3, 4, and 5.

FIG. 3 is a flow chart illustrating an example high level method 300 for automated analysis of cervix elastography for risk assessment of pre-term birth according to an embodiment of the present disclosure. Method 300 is described with regard to the systems and components of FIG. 1, though it should be appreciated that the method 300 may be implemented with other systems and components without departing from the scope of the present disclosure. Method 300 may be carried out according to instructions stored in non-transitory memory of a computing device, such as the image memory 120 of FIG. 1. In a non-limiting example, process 200 of FIG. 2 may be carried out according to method 300.

At 302, the method 300 includes acquiring ultrasound data of a patient. The ultrasound data may be acquired with an ultrasound probe (e.g., ultrasound probe 106 of FIG. 1). The ultrasound data may be processed to generate one or more displayable images, such as a cervical ultrasound scene comprising a plurality of frames, which may be displayed on a display device (e.g., display device 118). The ultrasound data may be processed to generate 2D images and/or 3D renderings that may be displayed in real-time as images are acquired and/or may be displayed in a more persistent manner in response to user input (e.g., an indication to freeze on a given image). The ultrasound data may include B-mode ultrasound data, and further, may include ultrasound elastography data, where tissue strain in a predetermined strain ROI is recorded and overlaid on the B-mode ultrasound data.

At 304, the method 300 includes receiving a user input indicating a cervix position on a selected displayed ultrasound image frame. The user input may be input manually by an ultrasound technician. For example, the ultrasound technician may indicate the position of the cervix in the cervical ultrasound scene via an input device in communication with the display and the ultrasound system, such as via the user interface input devices 115 of system 100. The operator of the ultrasound probe may be executing a patient exam according to an exam workflow that dictates making certain measurements of the cervix. The operator may indicate the cervix position via an input device of the display, such as an electronic stylus, a mouse, or a touchscreen. For example, the user may draw a line along the selected displayed ultrasound image indicating the cervix position (e.g., cervix position 216 of FIG. 2). As another example, the user may draw a box or a circle on the currently displayed ultrasound image indicating the cervix position, or indicate the cervix position in a different manner.

At 306, the method 300 includes generating a loss image (e.g., loss image 206) for an entire strain ROI. An example method for generating the loss image is described in more detail with reference to FIG. 4.

At 308, once the loss image is generated, the method 300 includes automatically selecting a background and a foreground of the cervical ultrasound scene, where the foreground may represent cervical tissue of interest and the background may represent surrounding cervical tissue (e.g., reference tissue) with which to compare the foreground region. The method may include selecting as the foreground, a first pixel within the foreground region of interest where the loss value is the largest. The method may include selecting as the background a second pixel within the background region of interest where the loss value is the lowest. Additionally, or alternatively, the foreground and the background may be selected by averaging of the loss values for a plurality of pixels inside a circle with a center pixel p (e.g., see FIGS. 9-10). In such an example, the first pixel may be the center pixel p in the foreground region of interest, and the second pixel may be the center pixel p in the background region of interest. In this way, the strain measurement may be more stable and less influenced by noise. A method for computing the loss image is described in more detail with reference to FIG. 5.

At 310, the method 300 includes automatically determining a softness ratio for each frame of the scene. In one example, the softness ratio is calculated from the strain values and may be the ratio of the average strain values of the foreground and the average strain values of the background. The ratio may be either the foreground strain/background strain or the background strain/foreground strain. Determining the softness ratio may include taking the ratio of the average strain value for pixels within the foreground, for all frames of the plurality of frames of the cervical ultrasound scene, and the average strain value for pixels within the background of all frames of the cervical ultrasound scene. In some examples, an alternative approach may include calculating the softness ratio based on single images and excluding the averaging part.

As an additional example, the softness ratio may be calculated based on shear wave imaging. For example, in shear wave imaging, elasticity values or values for a speed of sound are generated within a region of interest. If a sequence of shear wave images is acquired for the region of interest, then the method 300 may be applied similarly. In particular, instead of strain values, elasticity values or speed of sound values, may be used for calculating the loss function.

At 312, the method 300 includes automatically excluding outlier frames from downstream analysis, such as noisy frames and low-quality frames. In one example, outlier frames may be characterized by a high strain variance or by a low mean strain in the foreground area. Additionally, or alternatively, as strain estimation reliability is related to sufficiently correlated ultrasound signals, in some examples, correlation metrics may be used to determine low-quality frames. In another example, outlier frames may be determined based on the softness ratio determined for each frame and an average softness ratio determined for all frames of the scene prior to excluding outliers. As an example, outlier frames may be determined based on a quality threshold. The quality threshold may be a positive value non-zero threshold, such as a percent deviation from the average softness ratio for all frames of the scene prior to excluding outliers.

At 314, the method 300 includes determining an average softness ratio for all frames of the scene. In some examples, all frames may comprise the set of frames excluding outlier frames. Alternatively, the method may include calculating the mean of the foreground and the background strain, and then calculating the softness ratio.

At 316, the method 300 includes displaying results of the cervical elastography analysis. The results may include the average softness ratio for all frames of the scene. In some examples, all frames may comprise the set of frames excluding outlier frames. In some examples, a score or risk assessment of pre-term birth may be outputted based on the softness ratio, or in other examples, based on the softness ratio and additional medical factors such as a patient history.

FIG. 4 shows a flow chart illustrating an exemplary method 400 for generating a loss image as part of an automated analysis of cervix elastography for risk assessment of pre-term birth according to an embodiment of the present disclosure. In one example, the loss image may be determined based on a loss function, which operates at the level of individual pixels across a plurality frames comprising a cervical ultrasound scene. For each pixel, the loss function produces a corresponding loss value. In one example, the loss image may comprise a plurality of loss values determined using the loss function for each individual pixel for each frame of the cervical ultrasound scene. Method 400 is described with regard to the systems and components of FIG. 1, though it should be appreciated that the method 400 may be implemented with other systems and components without departing from the scope of the present disclosure. Method 400 may be carried out according to instructions stored in non-transitory memory of a computing device, such as the image memory 120 of FIG. 1. In a non-limiting example, the process 200 of FIG. 2 may be carried out according to method 400.

At 402, the method 400 includes extracting a region from a plurality frames comprising an ultrasound scene. In one example, as above, the region may be the strain ROI (e.g., strain ROI 228 of FIG. 2), which may be set manually by the technician prior to the cervical elastography examination. The extracting may be executed automatically by the processor of the ultrasound system with the only user input including the cervix position and the ultrasound imaging data acquired by the ultrasound technician.

At 404, the method 400 includes determining a loss value for each pixel of the region in the plurality of frames using a loss function. For example, method steps 406, 408, 410, and 412, described below, may be executed for each and every pixel within the extracted region of each and every frame of the scene. By determining loss values for the extracted region, as opposed to the entire scene, the approach may reduce processing time while achieving a high degree of stability.

At 406, the method 400 includes determining strain values for each pixel of the region, for each frame. The method may include defining a set Sp comprising a plurality of strain values for each pixel in the plurality of frames of the scene. In one example, the set may be calculated as follows:

$$S_p = \{s_p(i),\ i = 1, \ldots, n\} \tag{1}$$

where $s_p(i)$ is the strain value at pixel p in frame i. In other words, for each pixel p there is a corresponding strain value $s_p(i)$ for each frame i (e.g., from 1 to n) of the ultrasound scene.

At 408, the method 400 includes calculating a mean of the strain values $s_p(i)$ associated with pixel p across the plurality of frames, and at 410, the method 400 includes calculating a variance of the strain values $s_p(i)$ associated with pixel p across all frames.

At 412, the method 400 includes determining the loss value for each pixel of the set of pixels Sp, based on the mean and the variance of the strain values. The loss value is calculated for each pixel p as follows:

$$L_p = \text{Mean}(S_p) + \text{Var}(S_p). \qquad (2)$$

where Mean($S_p$) is the mean of the strain values of the set $S_p$, and Var($S_p$) is the variance of the set $S_p$. In other words, to calculate the loss value L for the pixel p, two components are considered: a mean strain and a strain variance, and the loss value of a given pixel may be a sum of the mean strain and strain variance for the pixel p of the set Sp.

In one example, in response to determining the loss value for each of the plurality of pixels of the cervical ultrasound scene, the method 400 may return. For example, the method 400 may return to method step 308 in FIG. 3. The loss values may also be used to select from the pixels of the scene a foreground or a background, as described below in reference to FIG. 5.

The method 500 illustrates an example of obtaining a loss function by calculating the mean and standard deviation of the estimated strain over a sequence of images. Another approach may include calculating several loss images, for example by using a narrow sliding window for calculation of the mean and standard deviation in temporal direction. Additionally, or alternatively, the loss function may be obtained by adding a weight to the mean and variance before summing, e.g., a weighted sum. As a further approach, the loss function may be obtained by computing a ratio of mean and variance, e.g., mean/variance.

FIG. 5 shows a flow chart illustrating an exemplary method 500 for selecting a background and foreground as part of an automated analysis of cervix elastography for risk assessment of pre-term birth according to an embodiment of the present disclosure. Method 500 is described with regard to the systems and components of FIG. 1, though it should be appreciated that the method 500 may be implemented with other systems and components without departing from the scope of the present disclosure. Method 500 may be carried out according to instructions stored in non-transitory memory of a computing device, such as the image memory 120 of FIG. 1. In a non-limiting example, process 200 of FIG. 2 may be carried out according to method 500.

At 502, the method 500 includes receiving a loss image. In one example, as above, the loss image may be determined based on a loss function, as described above in reference to FIG. 4.

At 504, the method 500 includes assigning a region of interest (ROI) based on a user input indicating a cervix position. For example, a foreground ROI (e.g., foreground region of interest 218 of FIG. 2) may be assigned based on proximity to the cervix position, such as within a first threshold proximity of the cervix position. Similarly, a background ROI (e.g., background region of interest 220) may be assigned based on proximity to the cervix position, such as within a second threshold proximity of the cervix position. In one example, the foreground region of interest may be closer to the cervix position and the background region of interest may a greater distance from, or larger area around, the cervix position. In one example, the method 500 may determine boundaries of the foreground ROI and the background ROI by analyzing results of manual cervix elastographic analyses performed by expert users. For example, data analytics using data acquired from expert users may provide a baseline assessment of a foreground and a background threshold to form the boundaries.

At 506, the method 500 includes selecting a foreground based on a largest loss value within the foreground region of interest. In one example, the method 500 may select a first pixel region comprising a plurality of pixels, e.g., 10 pixels, within the foreground region of interest where the loss value is the largest loss value based on the loss image. In other words, the foreground is selected such that the average strain value of the foreground is maximized in the entire foreground ROI.

At 508, the method 500 includes selecting a background based on a lowest loss value within the background region of interest. In one example, the method 500 may select a second pixel region comprising a plurality of pixels, e.g., 10 pixels, within the background region of interest where the loss value is the lowest loss value based on the loss image. In other words, the background is selected such that the average strain value of the background is minimized in the entire background ROI.

At 510, the method 500 includes displaying the background and the foreground selection to the user. For example, the first pixel region and the second pixel region may be overlaid on one of the frames of the cervical ultrasound scene via the display of the ultrasound imaging system.

At 512, the method 500 includes requesting user confirmation of the background and foreground selection. For example, the method may include generating a pop-up message that is displayed via the display of the ultrasound imaging system. The user may click a button to confirm or disconfirm one or both of the selected background and foreground. As used herein, a button may refer to any type of user input that provides a user a mechanism to select, confirm, or otherwise indicate a choice.

At 514, the method 500 includes determining whether the user confirms the selection. If the user confirms the selection, the method 500 may return. For example, the method 500 may return to method step 310 in FIG. 3.

At 516, if the user does not confirm one or both of the selected background and foreground, the method 500 may include prompting the user to manually input a background and/or foreground selection.

FIGS. 6-10 illustrate example user interfaces 600, 700, 800, 900, 1000 showing a sequence of actions performed within a method for automated analysis of cervical elastography for an exemplary ultrasound imaging system. The method for automated analysis of cervical elastography may be the same or similar to the series of actions described above with reference to FIGS. 2-5. Instructions for performing the method described in the user interfaces 600, 700, 800, 900, 1000 may be executed by a controller (e.g., controller 116) based on instructions stored in the memory (e.g., image memory 120) of the controller and in conjunction with feedback from components of the ultrasound imaging system (e.g., probe 106, user interface input devices 115, etc.) described above with reference to FIG. 1. In the examples, a user, such as an ultrasound technician, may interact with the user interfaces 600, 700, 800, 900, 1000 via one or more input devices, and the user interfaces 600, 700, 800, 900, 1000 may visually display user inputs and automated outputs of the automated analysis.

FIG. 6 shows a user interface 600. The user interface 600 may be displayed via a display screen 604 on display 602 of an ultrasound imaging system (e.g., system 100 in FIG. 1). The user interface 600 may display a cervical ultrasound scene or scene 612 that may be obtained by the ultrasound technician operating a probe (e.g., probe 106) during a cervical ultrasound. Further, the user interface 600 may display one-at-a-time a frame 606 of a plurality of frames comprising the scene 612. For example, the frame 606 may be displayed based on a user indication, such in response to a user scanning the scene 612 and selecting the frame 606 via an input device. Additionally or alternatively, the frame 606 may be displayed automatically, such as based on an image processing algorithm.

The user may indicate a cervix position on the frame 606 via the input device such as a display-linked electronic stylus. For example, the user may draw a line 608 on the display screen 604 indicating the cervix position. As another example, the user may draw a boundary 610 on the display screen 604 (e.g., an organic shape, a rectangle, etc.) indicating the cervix position. In one example, the cervical ultrasound scene 612 and the cervix position, as indicated by the line 608 or the boundary 610, may be the only user inputs to the automated analysis of cervical elastography. Based on the cervical ultrasound scene and in response to the user indicating the cervix position, the automated analysis of cervical elastography generates a loss image for a sub-region of the scene 612, shown in FIG. 7. For example, the loss image may be generated for the portion of the frame 606 within a strain ROI, which may be set manually by the technician before the examination.

FIG. 7 shows a user interface 700 displayed via the display screen 604 on the display 602 described above with reference to FIG. 6. The user interface 700 displays an automatically generated loss image 714. As above, the loss image 714 may be generated from a plurality of loss values, one loss value for each pixel, where the loss values are determined based on a loss function. Further, the user interface 700 displays the line 608 indicating the user-indicated cervix position. The line 608 is shown herein for reference; however in some examples, the line 608 may be excluded from the display subsequent to loss image generation. The automated analysis of cervical elastography may assign a foreground region of interest, displayed as a first shape 702. In one example, the foreground region of interest may be assigned, as above, based on proximity to the line 608 indicating the cervix position. For example, the first shape 702 may comprise an area of the loss image 714 within a first threshold proximity 704 of the line 608. In one example the first threshold proximity 704 may comprise a positive, non-zero number of pixels, a measurement of length, or other value.

FIG. 8 shows a user interface 800 displayed via the display screen 604 on the display 602 described above with reference to FIG. 6. As above, the user interface 800 displays the loss image 714. Further, the user interface 800 displays the line 608 indicating the cervix position. The automated analysis of cervical elastography may assign a background region of interest, displayed as a second shape 802. In one example, the background region of interest may be assigned, as above, based on proximity to the line 608 indicating the cervix position. For example, the second shape 802 may comprise an area of the loss image 714 within a second threshold proximity 804 of the line 608. In one example the second threshold proximity 804 may comprise a positive, non-zero number of pixels, a measurement of length, or other value, which may be a larger region around, or greater distance from, the line 608. As another example, the second threshold proximity 804 may comprise a region of a predetermined size that represents the area with the minimal loss function.

FIG. 9 shows a user interface 900 displayed via the display screen 604 on the display 602 described above with reference to FIG. 6. The user interface 900 displays the loss image 714 including the first shape 702 indicating the foreground region of interest assigned by the automated analysis of cervical elastography. The automated analysis of cervical elastography may select a foreground from within the foreground region of interest, displayed as a first circle 902. The foreground may be determined, as above, based on the loss image 714, where the foreground is selected such that the average strain value of the foreground is maximized in the entire foreground ROI. The first circle 902 includes a first pixel 904, shown as a small circle with a black dashed border, within the first shape 702 where the loss value is the largest based on the loss image 714. The first circle 902 may further include a plurality of adjacent pixels within proximity of the first pixel (e.g., 10 pixels).

FIG. 10 shows a user interface 1000 displayed via the display screen 604 on the display 602 described above with reference to FIG. 6. As above, the user interface 1000 displays the loss image 714 including the first shape 702 and the second shape 802, indicating the foreground region of interest and the background region of interest, respectively, assigned by the automated analysis of cervical elastography. The user interface 1000 displays the first circle 902 indicating the selected foreground including the first pixel 904. The automated analysis of cervical elastography may assign a background, displayed as a second circle 1002. The background may be determined, as above, based on the loss image 714, where the background is selected such that the average strain value of the background is minimized in the entire background ROI. The second circle 1002 may include a second pixel 1004, shown as a black dot, within the second shape 802 where the loss value is the lowest based on the loss image. The second circle 1002 may further include a plurality of adjacent pixels within proximity of the second pixel (e.g., 10 pixels).

In some examples, the user interface 1000 may display a pop-up 1006 requesting the user to confirm the background and foreground selection displayed as the first circle 902 and the second circle 1002, respectively. In response to the user confirmation, the automated analysis of cervical elastography may include computing a softness ratio based on the selected foreground and the background. For example, for each frame, the softness ratio may comprise the ratio of the average strain values of the foreground, e.g., within the first circle 902, to the average strain values of the background, e.g., within the second circle 1002. A final softness ratio may comprise the average of the softness ratio of all frames. The user interface 1000 may display the softness ratio on a pop-up 1008 of the automated analysis of cervical elasticity.

In this way, the disclosed systems and methods increase usability, minimize noise effects, accelerate processing, and reduce expert input reliance. The technical effect of the disclosed methods and systems for cervical elastography is increased processing efficiency. By using the loss image, which is generated for a portion of all frames of the ultrasound scene, the automated analysis focuses on tissues within proximity of the user-guided cervix position, as opposed to analyzing every pixel of all frames of the entire scene. The processing efficiency gains of the approach allow for determining the softness ratio from a large, stable dataset, thereby increasing accuracy and reproducibility.

The disclosure also provides support for a method comprising: acquiring an ultrasound scene comprising a plurality of frames, generating a first loss image for the plurality of frames, selecting a background and a foreground of the ultrasound scene based on the first loss image, and generating a softness ratio from the selected background and foreground. In a first example of the method, generating the first loss image comprises: extracting a region from the plurality of frames comprising the ultrasound scene, and for each pixel of the ultrasound scene: defining a set of pixels, determining a mean strain and a strain variance for the set of pixels, and determining a loss value that is a sum of the mean strain and the strain variance for the set of pixels. In a second example of the method, optionally including the first example, the set of pixels comprises a plurality of strain values for an individual pixel at each frame of the plurality of frames. In a third example of the method, optionally including one or both of the first and second examples, the method further comprises: a user input indicating a cervix position on the ultrasound scene, wherein the only user inputs are the ultrasound scene and the cervix position. In a fourth example of the method, optionally including one or more or each of the first through third examples, the method further comprises: assigning a foreground region of interest and a background region of interest based on proximity to the user input indicating the cervix position. In a fifth example of the method, optionally including one or more or each of the first through fourth examples, the foreground region of interest is closer to the cervix position than the background region of interest. In a sixth example of the method, optionally including one or more or each of the first through fifth examples, the method further comprises: selecting the foreground based on a largest loss value within the foreground region of interest and selecting the background based on a lowest loss value within the background region of interest. In a seventh example of the method, optionally including one or more or each of the first through sixth examples, the ultrasound scene comprises a cervical ultrasound scene. In a eighth example of the method, optionally including one or more or each of the first through seventh examples, the ultrasound scene comprises a sequence of shear wave images. In a ninth example of the method, optionally including one or more or each of the first through eighth examples, the generating the first loss image, the selecting the background and the foreground, and the generating the softness ratio execute automatically.

The disclosure also provides support for an ultrasound system comprising: an ultrasound probe, a display communicatively coupled to the ultrasound probe, a user input device communicatively coupled to the display, and a processor and non-transitory memory communicatively coupled to the display including instructions that when executed cause the processor to: acquire an ultrasound scene comprising a plurality of frames, receive a user input indicating a cervix position on the ultrasound scene, generate a first loss image for the plurality of frames, select a background and a foreground of the ultrasound scene based on the first loss image, and, generate a softness ratio from the selected background and foreground. In a first example of the system, the first loss image comprises a plurality of loss values, the plurality of loss values determined based on a sum of a mean strain and a strain variance for each individual pixel for each frame of the ultrasound scene. In a second example of the system, optionally including the first example, the instructions cause the processor to select the background and the foreground automatically. In a third example of the system, optionally including one or both of the first and second examples, the user input the cervix position and the ultrasound scene are the only user inputs. In a fourth example of the system, optionally including one or more or each of the first through third examples, the instructions cause the processor to select the foreground based on a largest loss value within a foreground region of interest and the background based on a lowest loss value within a background region of interest.

The disclosure also provides support for a method comprising: acquiring a cervical ultrasound scene comprising a plurality of frames, receiving a user input indicating a cervix position on the cervical ultrasound scene, generating a first loss image for the cervical ultrasound scene, assigning a foreground region of interest and a background region of interest based on the cervix position, selecting a foreground within the foreground region of interest and a background within the background region of interest based on the first loss image, determining a softness ratio for each frame based on average strain values in the foreground and average strain values in the background, and determining a final softness ratio based on an average softness ratio of all frames. In a first example of the method, generating the first loss image comprises: extracting a region from the plurality of frames comprising the cervical ultrasound scene, and for each pixel of the cervical ultrasound scene: defining a set of pixels, determining a mean strain and a strain variance for the set of pixels, and determining a loss value that is a sum of the mean strain and the strain variance for the set of pixels. In a second example of the method, optionally including the first example, the set of pixels comprises a plurality of strain values for an individual pixel at each frame of the plurality of frames. In a third example of the method, optionally including one or both of the first and second examples, the cervical ultrasound scene and the cervix position are the only user inputs. In a fourth example of the method, optionally including one or more or each of the first through third examples, the method further comprises: excluding outlier frames based the softness ratio of each frame.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:
1. A method comprising:
  acquiring an ultrasound scene comprising a plurality of frames;

generating a first loss image for the plurality of frames;

selecting a background and a foreground of the ultrasound scene based on the first loss image; and generating a softness ratio from the selected background and foreground.

2. The method of claim 1, wherein generating the first loss image comprises:

extracting a region from the plurality of frames comprising the ultrasound scene; and for each pixel of the ultrasound scene:

defining a set of pixels;

determining a mean strain and a strain variance for the set of pixels; and determining a loss value that is a sum of the mean strain and the strain variance for the set of pixels.

3. The method of claim 2, wherein the set of pixels comprises a plurality of strain values for an individual pixel at each frame of the plurality of frames.

4. The method of claim 1, further comprising a user input indicating a cervix position on the ultrasound scene, wherein the only user inputs are the ultrasound scene and the cervix position.

5. The method of claim 4, further comprising assigning a foreground region of interest and a background region of interest based on proximity to the user input indicating the cervix position.

6. The method of claim 5, wherein the foreground region of interest is closer to the cervix position than the background region of interest.

7. The method of claim 5, further comprising selecting the foreground based on a largest loss value within the foreground region of interest and selecting the background based on a lowest loss value within the background region of interest.

8. The method of claim 1, wherein the ultrasound scene comprises a cervical ultrasound scene.

9. The method of claim 1, wherein the ultrasound scene comprises a sequence of shear wave images.

10. The method of claim 1, wherein the generating the first loss image, the selecting the background and the foreground, and the generating the softness ratio execute automatically.

11. An ultrasound system comprising:

an ultrasound probe;

a display communicatively coupled to the ultrasound probe;

a user input device communicatively coupled to the display; and a processor and non-transitory memory communicatively coupled to the display, the non-transitory memory including instructions that when executed cause the processor to:

acquire an ultrasound scene comprising a plurality of frames;

receive a user input indicating a cervix position on the ultrasound scene;

generate a first loss image for the plurality of frames;

select a background and a foreground of the ultrasound scene based on the first loss image; and, generate a softness ratio from the selected background and foreground.

12. The ultrasound system of claim 11, wherein the first loss image comprises a plurality of loss values, the plurality of loss values determined based on a sum of a mean strain and a strain variance for each individual pixel for each frame of the ultrasound scene.

13. The ultrasound system of claim 11, wherein the instructions cause the processor to select the background and the foreground automatically.

14. The ultrasound system of claim 11, wherein the user input the cervix position and the ultrasound scene are the only user inputs.

15. The ultrasound system of claim 11, wherein the instructions cause the processor to select the foreground based on a largest loss value within a foreground region of interest and the background based on a lowest loss value within a background region of interest.

16. A method comprising:

acquiring a cervical ultrasound scene comprising a plurality of frames;

receiving a user input indicating a cervix position on the cervical ultrasound scene;

generating a first loss image for the cervical ultrasound scene;

assigning a foreground region of interest and a background region of interest based on the cervix position;

selecting a foreground within the foreground region of interest and a background within the background region of interest based on the first loss image;

determining a softness ratio for each frame based on average strain values in the foreground and average strain values in the background; and determining a final softness ratio based on an average softness ratio of all frames.

17. The method of claim 16, wherein generating the first loss image comprises:

extracting a region from the plurality of frames comprising the cervical ultrasound scene; and for each pixel of the cervical ultrasound scene:

defining a set of pixels;

determining a mean strain and a strain variance for the set of pixels; and determining a loss value that is a sum of the mean strain and the strain variance for the set of pixels.

18. The method of claim 17, wherein the set of pixels comprises a plurality of strain values for an individual pixel at each frame of the plurality of frames.

19. The method of claim 16, wherein the cervical ultrasound scene and the cervix position are the only user inputs.

20. The method of claim 16, further comprising excluding outlier frames based the softness ratio of each frame.

* * * * *